US012663413B2

(12) United States Patent
Uzu et al.

(10) Patent No.: US 12,663,413 B2
(45) Date of Patent: Jun. 23, 2026

(54) METHOD FOR MEASURING THE OXIDATION POTENTIAL OF SAMPLES, IN PARTICULAR AEROSOLS, EQUIPMENT FOR THE IMPLEMENTATION THEREOF AND USE OF SAME FOR ON-LINE ANALYSIS OF AIR QUALITY

(71) Applicants:CENTRE NATIONAL DE LA RECHERCHE SCIENTIFIQUE, Paris (FR); INSTITUT POLYTECHNIQUE DE GRENOBLE, Grenoble (FR); INSTITUT DE RECHERCHE POUR LE DÉVELOPPEMENT, Marseilles (FR); UNIVERSITE GRENOBLE ALPES, Saint Martin D'Heres (FR)

(72) Inventors: Gaëlle Uzu, La Tronche (FR); Jean-Luc Jaffrezo, Saint Martin le Vinoux (FR); Guilhem Freche, Grenoble (FR)

(73) Assignees: CENTRE NATIONAL DE LA RECHERCHE SCIENTIFIQUE, Paris (FR); INSTITUT POLYTECHNIQUE DE GRENOBLE, Grenoble (FR); INSTITUT DE RECHERCHE POUR LE DÉVELOPPEMENT, Marseilles (FR); UNIVERSITE GRENOBLE ALPES, Saint Martin D'Heres (FR)

( * ) Notice: Subject to any disclaimer, the term of this patent is extended or adjusted under 35 U.S.C. 154(b) by 507 days.

(21) Appl. No.: 18/251,975

(22) PCT Filed: Nov. 5, 2021

(86) PCT No.: PCT/EP2021/080824
§ 371 (c)(1),
(2) Date: May 5, 2023

(87) PCT Pub. No.: WO2022/096675
PCT Pub. Date: May 12, 2022

(65) Prior Publication Data
US 2024/0011971 A1 Jan. 11, 2024

(30) Foreign Application Priority Data
Nov. 6, 2020 (FR) ...................................... 2011431

(51) Int. Cl.
*G01N 33/497* (2006.01)

(52) U.S. Cl.
CPC ................................... *G01N 33/497* (2013.01)

(58) Field of Classification Search
CPC .... A61K 2300/00; A61K 35/74; A61K 45/06; A61P 35/00; C12N 15/74; C12N 9/50;
(Continued)

(56) References Cited

U.S. PATENT DOCUMENTS

| | | | |
|---|---|---|---|
| 2005/0142157 A1* | 6/2005 | Alimi | A61K 33/00 424/405 |
| 2022/0298461 A1* | 9/2022 | Zamarayeva | A61K 49/0093 |

OTHER PUBLICATIONS

Weber Samuël et al, "An apportionment method for the oxidative potential of atmospheric particulate matter sources: application to a one-year study in Chamonix, France", Atmospheric Chemistry and Physics, vol. 18, No. 13, Jul. 9, 2018 (Jul. 9, 2018), p. 9617-9629.
(Continued)

*Primary Examiner* — Jennifer Wecker
(74) *Attorney, Agent, or Firm* — WCF IP

(57) ABSTRACT
The present application relates to a method for the on-line and real-time automatic determination of the oxidization potential of an environment, enabling the air quality and/or the toxicity of the vapors emitted by various appliances or facilities to be analyzed.

14 Claims, 6 Drawing Sheets

(58) Field of Classification Search
CPC ............................... C12N 9/52; C12Y 304/24;
C12Y 304/24003; G01N 33/497; G01N
33/84
See application file for complete search history.

(56) References Cited

OTHER PUBLICATIONS

Calas Aude et al, "The importance of simulated lung fluid (SLF) extractions for a more relevant evaluation of the oxidative potential of particulate matter", vol. 7, No. 1.

Calas Aude et al, "Comparison between five acellular oxidative potential measurement assays performed with detailed chemistry on PM$_{10}$ samples from the city of Chamonix (France)", Atmospheric Chemistry and Physics, vol. 18, No. 11, Jun. 5, 2018 (Jun. 5, 2018), p. 7863-7875.

Moufarrej Lamia et al, "Assessment of the PM2.5 oxidative potential in a coastal industrial city in Northern France: Relationships with chemical composition, local emissions and long range sources", Aug. 6, 2020 (Aug. 6, 2020), vol. 748.

Barraza F et al, "Contrasts in chemical composition and oxidative potential in PM10 near flares in oil extraction and refining areas in Ecuador", Jan. 23, 2020 (Jan. 23, 2020), vol. 223.

Yu Haoran et al, "A semi-automated multi-endpoint reactive oxygen species activity analyzer (SAMERA) for measuring the oxidative potential of ambient PM 2.5 aqueous extracts", Aerosol Science and Technology., vol. 54, No. 3, Dec. 6, 2019 (Dec. 6, 2019), p. 304-320.

* cited by examiner

METHOD FOR MEASURING THE OXIDATION POTENTIAL OF SAMPLES, IN PARTICULAR AEROSOLS, EQUIPMENT FOR THE IMPLEMENTATION THEREOF AND USE OF SAME FOR ON-LINE ANALYSIS OF AIR QUALITY

The present invention relates to the analysis of the toxicity of ambient media, in particular aerosols, and more broadly to the analysis of air quality, or the toxicity of vapors emitted by various devices or installations (electronic cigarettes, stoves, vehicles, etc.).

Poor air quality is one of the leading causes of death in the world, and such health impact comes mostly from atmospheric particles: reactive oxygen species (ROS) are brought by such pollution and/or produced in the lungs by reactions with the chemical components breathed in. Some of the reactive species can be neutralized by anti-oxidant cellular defense mechanisms. However, the reactive species are responsible for oxidative stress, when lung defense thresholds are exceeded by the amount of such species. Such oxidative stress is the common denominator of the main cardio-respiratory diseases observed during exposure to air pollution.

In all countries, regulations, where regulations exist (and which are supposed to protect populations from such impacts) are based on the mass of atmospheric particles (usually PM10 or PM2.5: particles with a diameter of less than 10 or 2.5 μm). However, the mass does not take into account the main characteristics of PM responsible for the health effects thereof: size distribution, chemistry, solubility, surface state, etc.

Thus, the measurement of oxidative potential (OP) is also considered to evaluate the health effects of air quality, or of pollutant emissions. OP is defined as the ability of a sample to oxidize the lung environment, through the generation of reactive oxygen species and/or through the consumption of antioxidants. Such OP measurement thus evaluates the ability of polluting particles and gases to generate oxidative stress on the lungs.

The current measurements of OP are very generally carried out from atmospheric samples on filters, then analyzed in the laboratory.

However, filter technology involves a high detection limit, requires the collection of material in high quantities and thus requires long exposure times and then long filter processing times.

E.g., Weber Samuel et a/Atmospheric Chemistry and Physics, vol. 18, no. 13, 2018, 9617-9629 and Calas et a/Scientific Reports, vol. 7, no. 1, 2017 or Calas et al vol. 18, n+11, 2018, (7863-7875) describe measurement methods comprising a sampling on filters and requiring a long exposure time and incompressible time-frames for collection, extraction and analysis.

Thereby, Yu et al Aerosol science and technology, vol. 54, 304-320, 2020 describes a semi-automatic analysis of the OP of samples which are nevertheless prepared in the laboratory, after the extraction of the filters brought from the collection site. In addition, a single sample is subject to a plurality of consecutive tests, resulting in a significant increase in the time of acquisition of the results.

With such methodologies, whether automated or not, a significant time-frame results between the sampling and the result of the analyses carried out. For the above reason, no health decision can be made in real-time.

On-site automatic measurements in real-time (i.e. "on-line") could be used for systematizing the monitoring of air quality or of emissions, for proposing health or industrial warning possibilities, which would moreover be done on bases effectively linked to the harmfulness of the sampled media, and in particular for PM, not related just to the amount thereof in the atmosphere.

To date, the research methods used on-site ("on-line") and brought to the prior art implement analyses which cannot be used for obtaining sufficiently precise quantifications for ambient atmospheric media which are e.g. close to the regulations in force in Europe.

It is thus essential to provide an automatic and real-time method, reliable and reproducible in order to provide health control, for the determination of the OP of samples, in particular of aerosols, such as atmospheric samples or pollutant emissions. Moreover, detection thresholds have to be sufficiently low to be used for a determination under conditions generally encountered in the atmospheres of developed countries.

Moreover, it is important to determine the OP under conditions which are as representative as possible of physiological conditions.

Automatic "on-line" measurements would make it possible to determine in real-time the sources of pollution episodes. The measurements would also help to better target regulations (and redirect air pollution policy) to the sources which are most harmful to respiratory health. The measurements would also make it possible to efficiently test, in the laboratory or on site, the emissions of any polluting or depolluting process.

The present invention thus proposes a method for automatically measuring OP "on-line", and the corresponding equipment.

According to a first subject matter, the present invention relates to a method for measuring the oxidizing potential (OP) of a test environment, comprising:

Collecting a sample from said test environment,

Mixing the test sample or a fraction thereof with an artificial lung fluid sample, so as to obtain a liquid test sample, Conducting of one or a plurality of parallel oxidative potential quantification tests on said liquid test sample, Determining the oxidizing potential of said test environment.

Oxidative potential (OP) refers to the ability of a sample to oxidize the lung environment, by supplying or generating reactive oxygen species which consume the antioxidants of the environment.

The test environment can be, in particular, an aerosol.

The term "aerosol" defines according to the present invention, a mixture of particles suspended in a gas. The particles can be either identical or different in terms of the chemical composition or the physical and chemical characteristics thereof.

Typically, the test environment is the ambient air or the atmosphere at the outlet of a device or installation emitting particles (industrial processes, vehicles, electronic cigarettes, chimneys, etc.) or seeking to depollute the ambient air or a device or installation with polluting emissions.

The expression "test environment" refers to the environment to be tested.

The term "test sample" refers to a sample of the test environment. The test sample thus contains a gaseous fraction and/or a particulate fraction. The test sample can be analyzed as is. Alternatively, the gas phase and/or the particulate phase of the sample can be analyzed alone, by means of separation methods, in particular separation methods already existing on the market.

Typically, the test sample or the particulate fraction thereof consists of particles of specified size. Any size fraction can be considered, depending on the method used at the input of the instrument. According to one embodiment, the sample corresponds to the $PM_{2.5}$ or $PM_{10}$ fraction (particles with a diameter less than 2.5 or 10 μm, respectively).

The test sample can be taken by any method, in a reaction chamber, such as a nebulizer chamber, e.g. by aspirating in a specified quantity of the environment to be tested.

Typically, sampling can be carried out by a cyclone when the test environment is e.g. an aerosol.

A cyclone can be used for obtaining an aerosol sample consisting of particles in a gas thereof, according to the aerodynamic diameter (Dae) of said particles. The fine particles, of lower inertia, move less away from the axis of the cyclone and are driven by an ascending vortex towards an axial outlet situated in the upper part of the cyclone where the particles are collected. The cyclone is thereby used for performing a particle size classification. Typically, the flowrate of the cyclone pump can be comprised between 1 and 10 I/minute, typically about 5 I/minute.

According to one embodiment, the method comprises, after the sampling step and before the mixing step, the step of fractionating the test sample into a gaseous fraction and/or a particulate fraction.

Such step can be carried out by means e.g. of a denuder

Typically, the fraction can be the particulate fraction $PM_{2.5}$.

The test sample or a fraction thereof obtained in the case of fractionation, as discussed above, is then mixed with a liquid phase mimicking the lung environment. According to the invention, the liquid phase is an artificial lung environment. According to one embodiment, the Gamble solution, is concerned, as described by Marques et al Dissolution Technologies 15-28, 2011.

The Gamble solution typically comprises:
0.095 g/l magnesium chloride,
6.019 g/l sodium chloride,
0.298 g/l potassium chloride,
0.126 g/l disodium hydrogen phosphate,
0.063 g/l sodium sulphate,
0.368 g/l calcium chloride dihydrate,
0.574 g/l sodium acetate,
2.604 g/l sodium hydrogen carbonate,
0.097 g/l sodium citrate dihydrate in water.
Typically, the Gamble solution has a pH of 7.4.
In the respiratory environment, such lung interstitial fluid is pressed against the walls of the respiratory system by means of a surfactant, 1,2-dipalmitoylphosphatidylcholine (DPPC). Since it is known that surfactants act on the solubility of particles in general and in order to get as close as possible to physiological conditions, the Gamble solution is advantageously supplemented with surfactant, such as 1,2-dipalmitoylphosphatidylcholine (DPPC), typically at a concentration of about 0.02% (concentration measured in the respiratory system)

The artificial lung environment according to the invention is thus distinguished in particular from the environment used by Yu et al Aerosol Science and technology, 2020 (supra) in that the fluid used by Yu et al ("surrogate lung fluid") is just a mixture of antioxidants the depletion of which is then measured by the authors.

The liquid phase can be obtained by nebulization. Typically, nebulization comprises the projection of fine droplets of the artificial lung environment and the test sample or a fraction thereof, so as to obtain a liquid phase comprising the particles and/or the soluble gases, mixed into the artificial lung environment.

Typically, the artificial lung environment and the liquid test sample are maintained at conditions representative of physiological conditions, in particular with a temperature comprised between 30 and 40° C., typically about 37° C., and/or a pH maintained between 7 and 8, in particular at 7.4.

The liquid test sample obtained can be either a suspension or a solution:

When the test sample is not fractionated, the liquid test sample resulting from mixing is a suspension.

The term "suspension" refers to any dispersion of a solid in a liquid.

When the test sample is fractionated and the particulate fraction is used, the liquid test sample resulting from mixing is a suspension.

When the test sample is fractionated and the gas fraction is used, the liquid test sample resulting from mixing is a solution.

The liquid sample thus obtained is then subject to one or a plurality of tests of quantification of the oxidizing potential thereof.

"Oxidative potential quantification test" means a test measuring the consumption by the test sample of a given antioxidant species.

In short, such tests are based on measuring the depletion of the antioxidant species when the species is brought into contact with the sample to be tested. The depletion of antioxidant species (when in excess) is proportional to the concentration of reactive species in the test sample.

A plurality of tests, each based on a separate antioxidant species, can be conducted in parallel.

For each test conducted alone or in parallel, a calibrated volume fraction of the sample is used, said fraction being calibrated by sampling with a syringe pump in the reaction chamber. The unused volume being discharged at the end of the reaction to a recovery bin.

Typically, at least two different test lines are conducted in parallel. Each test line comprises the mixing of a specified amount of the liquid test sample with a specified amount of the antioxidant species of the test under consideration. Advantageously, the test lines are based on antioxidant species which are complementary in that same react in distinct ways to the reactive species of the test environment.

Antioxidant species include:
ascorbic acid (AA),
dithiothreitol (DTT),
dichlorofluorescein (DCFH),
gluthatione (GSH),
RTLF mixture (respiratory tract lining fluid, is a mixture of AA, GSH and uric acid)

The reaction mixture considered is generally produced under physiological conditions (temperature of about 37° C., and pH maintained between 7 and 8, in particular at 7.4), and preferentially protected from light. Generally, the incubation of the test sample with the antioxidant species is conducted for a period comprised between 5 minutes and 1 h.

According to one embodiment, before measuring the reactivity of the sample, two pre-measurements are carried out and will be subtracted from the measurement of the sample when calculating the oxidizing potential thereof:

A measurement of the intrinsic absorbance/fluorescence of the test sample alone

A "blank" measurement of the instrument which consists of measuring the absorbance/fluorescence of the antioxidant without the presence of a test sample which is replaced by ultra-pure water.

After incubation, the decrease in the concentration of the antioxidant species in the reaction mixture (consisting of the liquid test sample and a determined quantity of an antioxidant species) is determined by optical measurement, in particular by spectrophotometry (absorbance, UV-visible, fluorescence, etc.). The optical data obtained can be collected on a computer using the control interface (e.g., in LabVIEW). Such data can be used for computing the amount of ROS generated in the presence of the test sample analyzed after subtraction of blanks and calibration of the instrument:

The consumption of antioxidant species by the sample (per unit volume of the test environment or per unit mass of the test sample) is correlated with the concentration of reactive oxygen species in the sample.

The concentration of reactive species is then correlated with the OP of the test sample, and ultimately with the tested environment.

After measurement, the liquid flow is purged to the outside of the system.

More precisely, the tests can be carried out by application or adaptation of the methodologies described by Calas et al Scientific reports 7, 11617, 2017.

Typically, the methodology comprises first the measurement of the intrinsic absorbance of the liquid test sample at the desired wavelength, UV or visible, and then a quantity of the antioxidant species is injected into the liquid test sample and into a blank sample (ultra-pure water). In each case, the concentration of the antioxidant species is then quantified at a plurality of time intervals after mixing. The remaining amount of antioxidant species at the end of exposure (typically after a reaction time of about 30 minutes with the sample) can either be read directly by absorbance or fluorescence or assayed. Typically, for DTT, the remaining amount can be assayed with 5,5-dithiobis(2-nitrobenzoic acid) (DTNB).

The rate of depletion of antioxidant species ($nmol·minute^{-1}$) is determined from the linear regression slope of the concentration of antioxidant species (nmol) vs. the time of contact with the sample. The intrinsic absorbance is then subtracted from the final absorbance, and the loss antioxidant species of the blank (ultra-pure water) is subtracted from the loss of antioxidant species of the sample, so as to obtain the effective depletion of the antioxidant species of the sample.

The RTLF test is based on a synthetic mixture containing equimolar concentrations of ascorbic acid (AA), urate (UA) and reduced glutathione (GSH). The analysis of GSH is obtained from the analysis of total gluthatione and oxidized glutathione (GSSG), by modification of the method described by Baker et al Anal. BioChem. 190, 360-365, 1990, with the reagent of Ellman's (DTNB, 5,5-dithiobis(2-nitrobenzoic acid). The product formed, the yellow thio-2-nitrobenzoic (TNB), exhibits an absorbance peak at 412 nm.

According to one embodiment, the method according to the invention implements the OP quantification test by measuring the depletion of ascorbic acid (AA), and optionally the OP quantification test by measuring the depletion of dithiothreitol (DTT).

For AA, the test is based on AA consumption, followed by UV spectrophotometry (at 265 nm).

For DTT, the test is based on the consumption of DTT, the amount remaining after exposure with the sample is determined with 5,5-dithiobis(2-nitrobenzoic acid) (DTNB) and monitored by visible light spectrophotometry (at 412 nm).

For the DCFH (2',7'-dichlorodihydrofluorescein diacetate) test, the depletion is monitored by fluorescence spectrometry (excitation 485 nm, emission 530 nm).

The determination of the oxidizing potential of said test environment is carried out by recalculating the OP of the initial test environment from the OP obtained from the test sample thus obtained.

The method according to the invention can be fully automated and carried out on the site of collection ("on-line" implementation) of the test sample. An intermediate extraction of the collected samples is not necessary, as is required for filter-collected samples. In fact, the measurement and quantification of the OP can be obtained in near real-time with a real-time goal.

Indeed, filter technology requires a sample processing time and thus differs with regard to the time of access to results, even in the case of automation.

Moreover, the method according to the invention makes possible a detection limit on the order of $3.10^{-3}$ $nmol·minute^{-1}$ for the AA test and of $10^{-5}$ $nmol·minute^{-1}$ for the DTT test. By convention, the detection limit is determined as three times the standard deviation of the blanks measured with ultra-pure water. The expression of the detection limit as a function of the mass concentration of PM in the atmosphere is impossible because same depends on the reactivity of the atmospheric mixture present at the time when the measurement is made. Thereby the instrument will be apt to be sensitive to very low concentrations near a source of very oxidizing particles but higher for places with less oxidizing species in the atmosphere. For the above reason, research groups use said common denominator. The detection limit can also be calculated for known reference compounds found in the atmosphere. As an example, the equipment can detect $5.10^{-4}$ µM of Cu ($CuCl_2$ solution) for the AA line and $1.10^{-4}$ µM of Cu for the DTT line.

Such detection limits are advantageously distinguished from technologies involving filters which require detection limits typically on the order of $10^{-2}$ $nmol·minute^{-1}$ for the AA test and $10^{-3}$ $nmol·minute^{-1}$ for the DTT test.

OP is a health indicator (the results of which correlate with toxicological tests on the same samples) of air pollution or emissions.

According to another subject matter, the present invention thus further relates to a method for determining atmospheric pollution or gas and/or particle emissions, said method comprising:

The implementation of the method for determining the OP of the test environment according to the invention from a test sample taken from ambient atmospheric air or the emissions of gases and/or particles to be tested;

The correlation of the OP obtained with the air quality or toxicity of the tested environment.

More particularly, said correlation can in particular comprise the comparison of the value of the OP thus obtained with the value of samples which were already characterized.

The method according to the invention can thus be used for the real-time measurement of the health exposure to atmospheric pollution, i.e. in a period of time of about one hour, or less.

Such measurement of reactivity can be associated with a plurality of physical and chemical properties (composition, size, solubility, speciation, etc.) of the samples, according to the results obtained according to the antioxidant species used for the tests.

Thereby e.g. the ascorbic acid test is indeed selective with regard to metals in particular and the DTT test is sensitive, in a balanced way, to many organic and inorganic compounds.

The method according to the invention finds an application thereof in particular for the monitoring and, if appropriate, the prediction of air quality by the organisms which carry out the measurements.

The method can also be advantageously used in various industrial applications for testing pollutant emissions generated by different devices or installations (industrial processes, motor vehicles, wood stoves, manufacturing processes, etc.) or for testing depollution techniques (filtration, etc.).

According to another subject matter, the present invention further relates to an instrument for the automatic on-line determination of the OP of a test environment, comprising:

a module for collecting a test sample from the test environment;

a nebulizer chamber of at least a fraction of the test sample with an artificial lung fluid sample, so as to form a liquid test sample;

at least one test module configured for reacting the resulting liquid test sample with a reagent;

a module for measuring the depletion of said reagent;

a module for calculating the OP.

In one embodiment, said instrument can further comprise a system configured for feeding the test module(s):

with a liquid test sample from the outlet of the nebulizer chamber, with a reagent from a reagent storage tank.

According to one embodiment, the instrument can further include one or a plurality of test modules in parallel, each test module being configured for reacting the liquid test sample with a respective reagent.

Typically, the measurement module comprises an optical measurement system.

According to one embodiment, the instrument can further comprise a system configured for circulating a wash solution through the at least one test module.

FIGURES

Figure 1:
FIG. 1 represents an operating diagram according to an embodiment of the method and of the instrument according to the invention.

According to the invention, FIG. 1 illustrates the succession of the following 4 modules:

a sample preparation module 1 comprising a collection module, e.g. a cyclone 11 and a nebulizer chamber 13;

a test module 2;

a measurement module 3; and a calculation module 4.

According to one embodiment, the function of the sample preparation module 1 is to prepare a liquid test sample from an environment to be tested, such as an aerosol. To this end, a collection module 11 extracts the test sample, e.g. an aerosol test sample, into a reaction chamber. The reaction chamber can be a cyclone effect module, and the particles contained therein are extracted from the aerosol environment to be tested, depending on the size of the particles.

A denuder 12 or high efficiency air filter can be present between the collection module 11 and the nebulizer chamber 13, for limiting the aerosol test sample to either the particle fraction or the gas fraction.

The test sample or a fraction thereof thus collected is led into a nebulizer chamber 13 where the test sample is brought into contact with an artificial lung fluid sample. The liquid test sample thus obtained is then conveyed to the test module 2.

According to one embodiment, a system 16 such as a syringe pump draws the liquid test sample at the outlet of the module 1 to the test module.

The system 16 also takes a reagent sample stored in a tank 14, for being reacted with the liquid test sample. Control measurements, not shown in FIG. 1, are carried out in parallel.

Between two samples taken by the system 16, a washing solution stored in the container 15 is sampled by the system 16 and then discharged into the waste recovery tank 10.

As shown in FIG. 1, a plurality of test modules 2 can be present in parallel, each test being conducted with a given reagent. In such configuration, a determined fraction of the liquid test sample is taken by the system 16 to be reacted with a given reagent.

The test module 2 is advantageously maintained under physiological conditions:

Typically, the temperature is maintained between 30 and 40° C., typically at about 37° C. Generally, the pH is maintained between 7 and 8, in particular at 7.4

At the end of the test, the system 17, typically a pump, such as a peristaltic pump, conveys the reaction mixture from said test to the measurement module 3.

The data can be acquired, in particular, on a portable wide spectrum spectrophotometer.

The measurement module 3 typically comprises an optical measurement system 19 such as a spectrophotometer e.g., for measuring an optical property (such as e.g. absorbance or fluorescence) of the reaction mixture by means of a light source 18.

The optical measurement is then processed in the calculation module 4:

According to calculation algorithms, the optical measurement leads, ultimately, to the value of the oxidizing potential of the test environment: The value can first be correlated with the concentration of reagent after incubation, according to the Beer-Lambert law. The concentration of the reagent in the reaction mixture after incubation can be used for determining the depletion of reagent with respect to the quantity of reagent injected into the test module 2. Such depletion is attributable to the concentration of reactive oxygen species present in the test sample or in a fraction of the test sample. The oxidizing potential of the mixture tested can be associated with said value.

The calculation module 4 can further comprise a data processing system 20

EXAMPLES

A measuring instrument according to the invention has been produced, with the following specifications:

Maximum dimensions: Approx. 50*40*30 (L*D*h), Weight: 20 kg

Air flow-rate: 1 m3/h

Autonomy: 1 day

Power consumption: <800 W·h

Measurement frequency: 1 integrated measurement over 40 minutes per hour.

Measuring range: from 0.05 to 25 nmol of antioxidant AA·minute$^{-1}$, over a linear range Repeatability across the range: <10%

Equipment blank (LOD) approx. 5 pmol of antioxidant AA·minute$^{-1}$

Contamination of measurements by hysteresis: less than 3%

Autonomy of consumables on the order of 3 to 4 days

The aerosol environment to be tested was the ambient air of the laboratory wherein the instrument according to the invention is placed.

The test aerosol sample was taken by a pump and all of the aerosol was taken successively for 10, 20 and 30 minutes at 5 I·minute$^{-1}$.

During the pumping time of the sample, a blank is made: a solution of water $H_2O$ is injected and then a solution composed of ascorbic acid (AA)+$H_2O$ is injected. The blank is passed through the measurement module (typically a flow-cell or a cuvette), before plotting the absorbance spectrum of the solution. Such reference provides an initial value to subtract from the samples. Once the reference was produced, 1 ml of sample is brought into contact with 1 ml of AA and sent to the measuring cell:

For the sample, the absorbance at 265 nm is acquired as a function of time and the acquisition starts if the following two conditions are met: a temperature of 37.2° C.+/−0.2° C. and an intensity >12,000. The device is then rinsed device 3 times with 0.1% nitric acid so that there is no longer any presence of polluted solution in the syringe.

Figure 3:
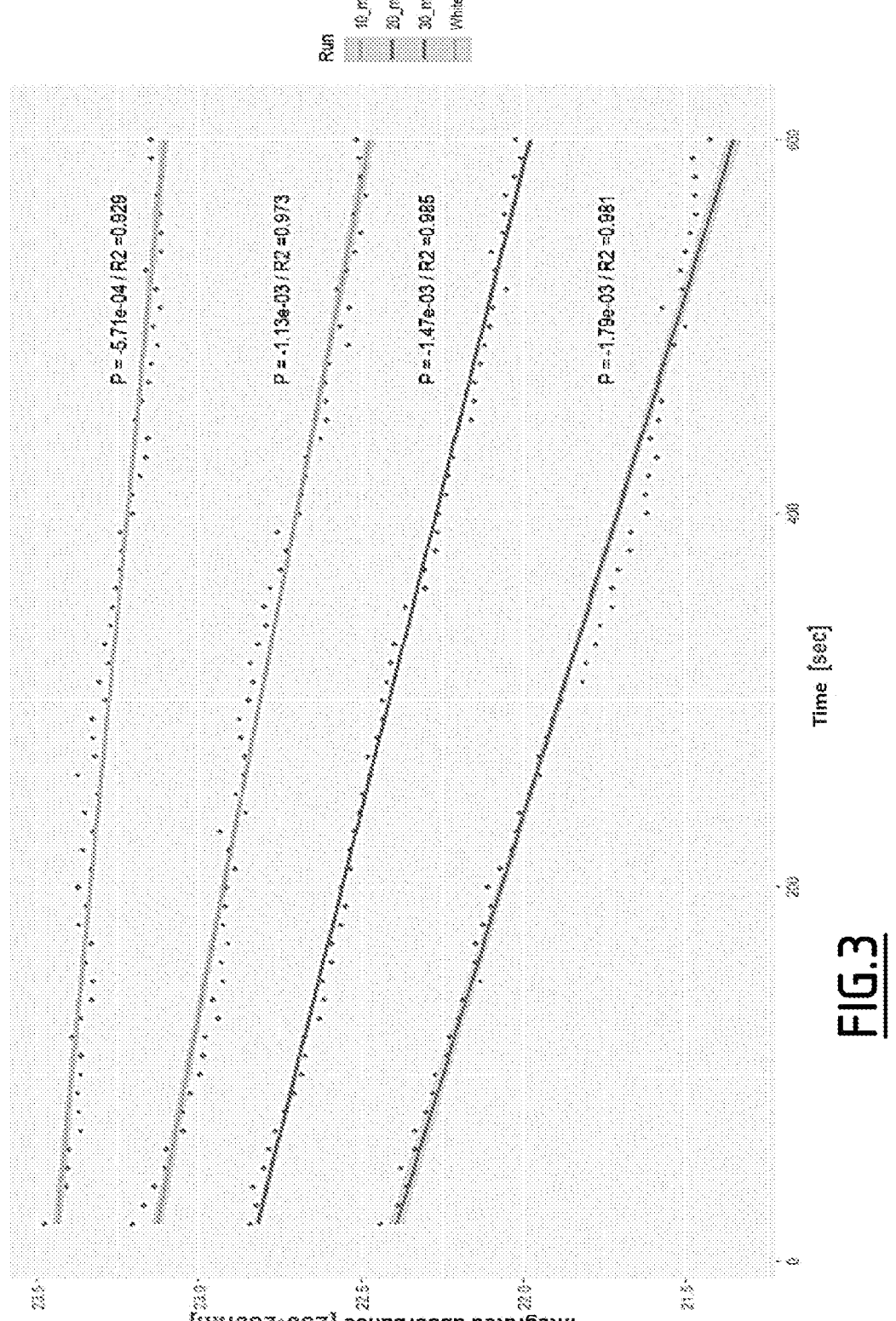
FIG. 3 represents the reactivity of the test environment (ambient aerosol environment of the laboratory) for different sampling times.

The results were obtained between 20 and 40 minutes for one cycle and are illustrated in FIG. 3. The slope, i.e. the reactivity of the sample increases as the concentration thereof increases, i.e. when the sampling time in the ambient air of the laboratory is longer. The detection limit was measured at 4.1 pmol·minute$^{-1}$ for the AA test.

Figure 6:
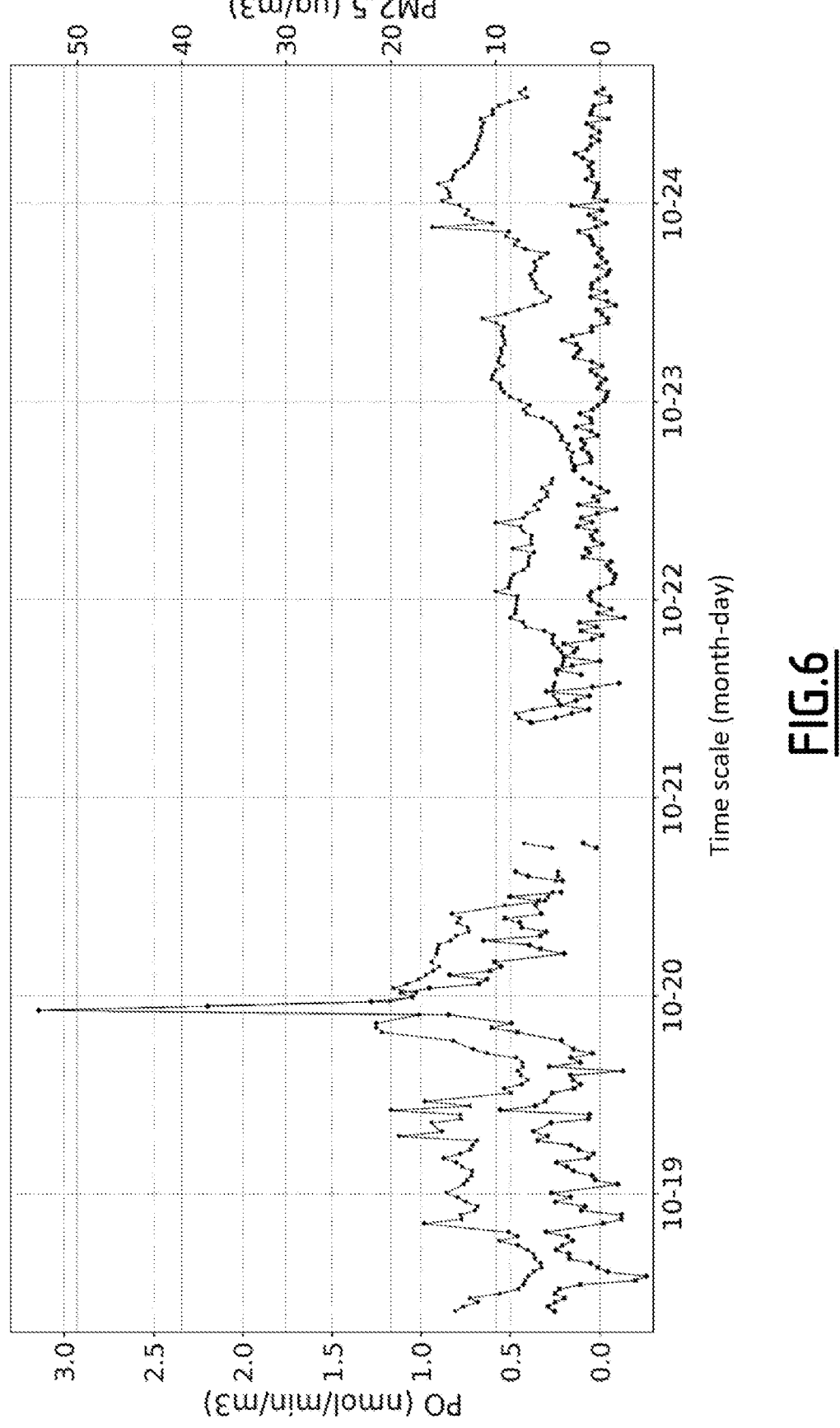
FIG. 6 represents measurements of the oxidizing potential (AA test, lower curve) as a function of a time scale (month-day), using the method according to the invention (ROS on-line) equipped with a PM2.5 head, situated on the roof of the IGE (Grenoble). The co-localized d mass measurements (upper curve) are carried out by a GRIMM particle counter.

The invention was also deployed in the ambient air of the city of Grenoble, for a few days. The results are shown in FIG. 6. During the period covered by said figure, the mass concentrations are particularly low, below 10 µg/m$^3$ on average over the last days of the campaign (the current European regulation requires to not exceed 25 µg/m$^3$ as an annual average). The sampling time step of 30 minutes, the continuity of the measurement series (except for a period related to the lack of reagents in the middle of the graph), values close to zero of the instrument during periods of very low mass concentrations, and a peak of OP totally synchronous with a peak of mass in the middle of the night, over a period of 1h30, should be all noted. The last observation is particularly interesting, and shows the sensitivity of the instrument, the interest of the measuring time step, the low hysteresis of the signal, and the aptitude to follow "rapid" episodes.

Comparative Examples

1. By comparison, the process described by Yu et al Aerosol Science and technology, Vol. 54, 304-320, 2020 leads to results (5 tests on the same sample) on the order of 4 hours for a cycle, with a detection limit of 0.197 µM·minute$^{-1}$ for ultra-pure water blanks, when the detection limit of our instrument is 4.1 µM·minute$^{-1}$ in less than 30 minutes.

Figure 2:
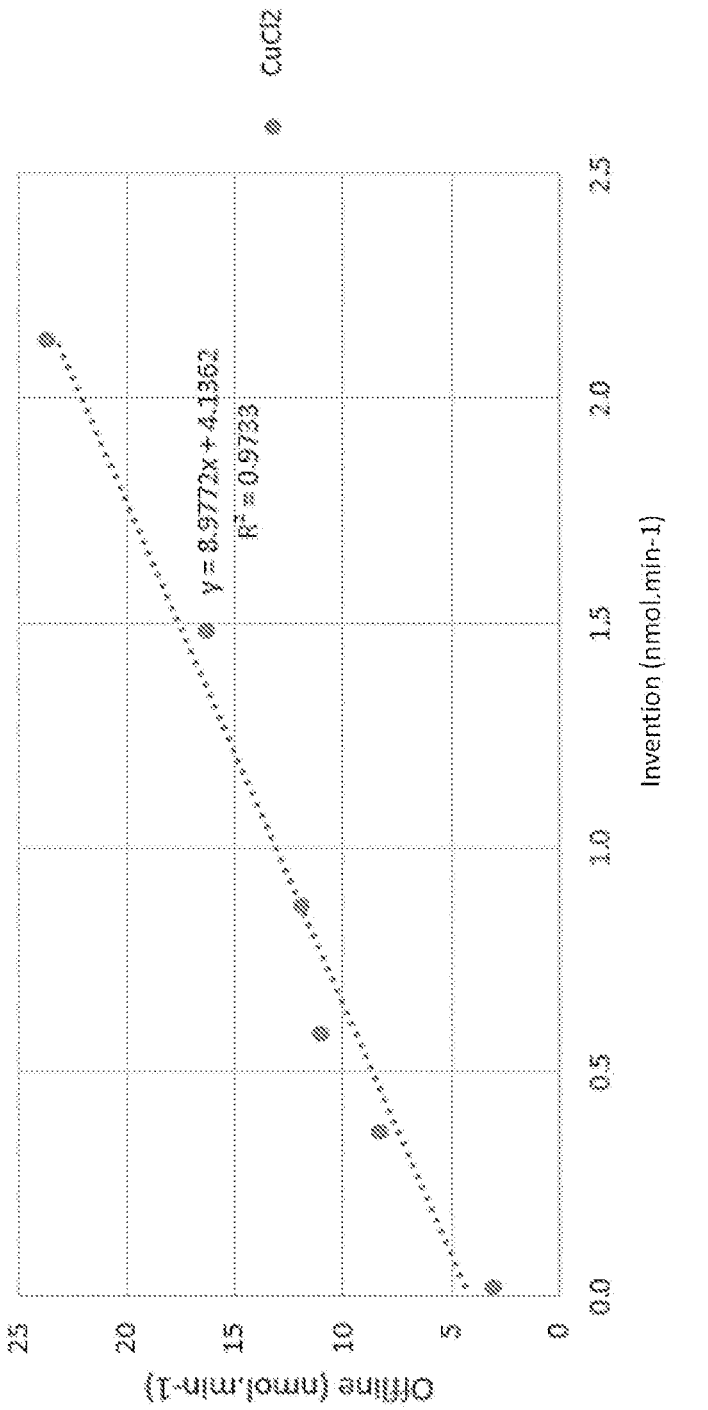
FIG. 2 shows the correlation between the results obtained with the on-line method of the invention, compared to the filter measurement method.

2. The "on-line" process according to the invention was also compared to the "off-line" processes used for taking measurements on filters (typically by plate spectrophotometry), for different atmospheric compounds. The results are illustrated in FIG. 2 for a copper compound ($CuCl_2$) at concentrations typical of the concentrations encountered in the atmosphere. For the same concentrations of copper, the oxidizing potential was measured with the AA test with a plate spectrophotometer in the laboratory, or with the invention. The results are similar between the two processes for concentrations between 0.1 and 5 µM of $CuCl_2$ comprising extreme values of copper encountered in the atmosphere (correlation close to 1 for 6 points (6 concentrations tested); slope of the regression line close to 1; very low ordinate at the origin).

Figure 4:
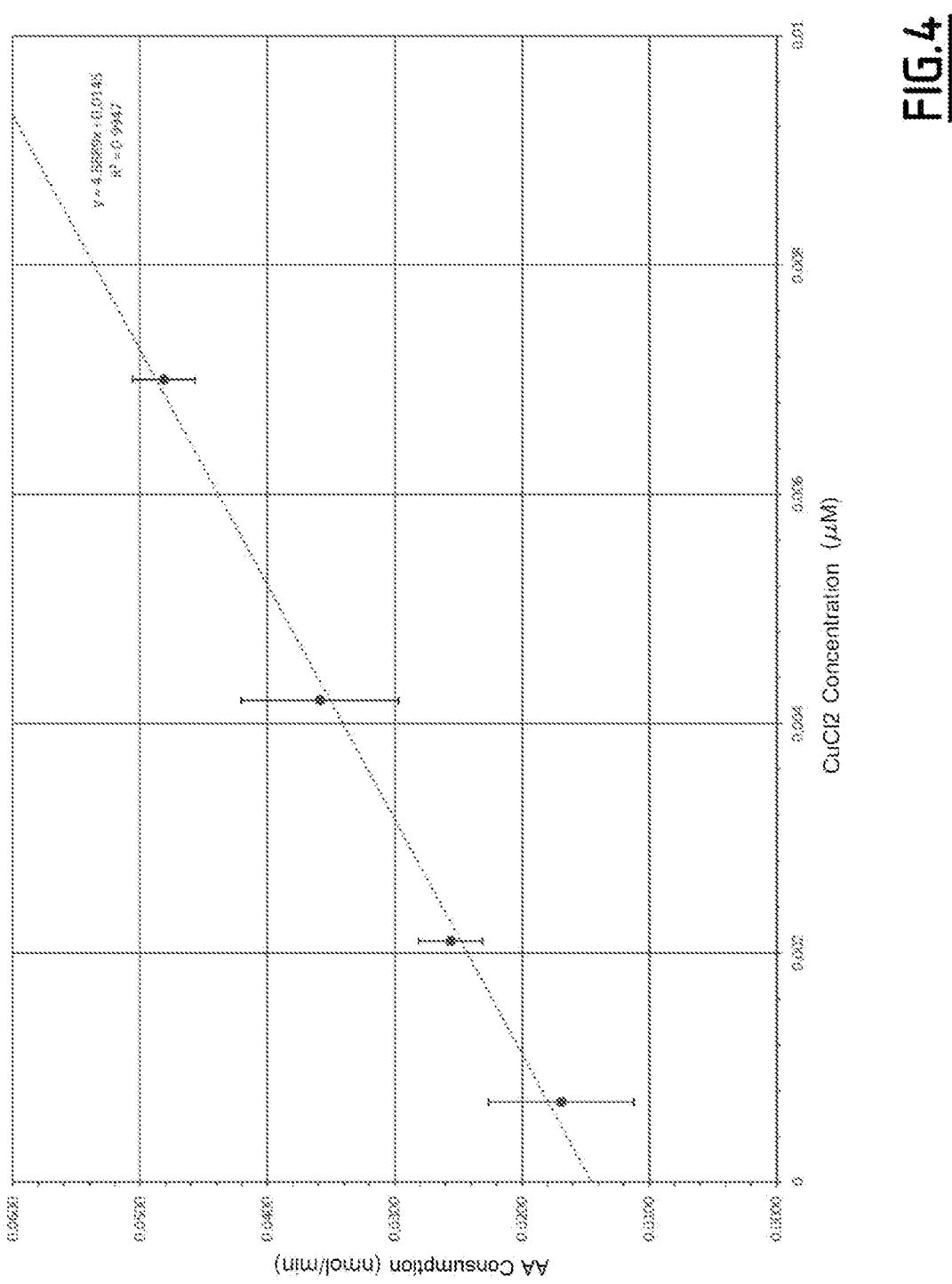
FIG. 4 represents the response of the instrument for the AA for $CuCl_2$ ranges between 0.001 $\mu mol \cdot l^{-1}$ and 0.01 $\mu mol \cdot l^{-1}$, i.e. concentrations representative of the atmospheric concentrations of copper, as found in European cities (5-20 $ng \cdot m^{-3}$).
Figure 5:
FIG. 5 shows the response of the instrument for the DTT line for $CuCl_2$ ranges between 0.001 $\mu mol \cdot l^{-1}$ and 0.02 $\mu mol \cdot l^{-1}$, i.e. concentrations representative of atmospheric concentrations of copper, as found in European cities (5-20 $ng \cdot m^{-3}$).

3. Sensitivity limit tests of the on-line invention were also carried out, for each measurement line of the invention, with a linearity range for copper, an atmospheric reference compound known for the oxidizing power thereof. The results are shown in FIG. 4 for the AA measurement line and in FIG. 5 for the DTT reagent measurement line. As a comparison, the range of copper concentration which was measured in the ambient air in an urban background was between 0.001 and 0.016 µM (range of concentrations based on observations in the ambient air of the city of Grenoble, year 2017-2018, 1 measurement every 3 days representing concentrations between 8 ng/m$^3$ in the urban background and 80 ng/m$^3$ next to a boulevard). Thereby, the two figures show that the invention is suitable for detecting realistic concentrations of atmospheric copper.

The invention claimed is:

1. A method for measuring the oxidative potential (OP) of a test environment, comprising:

collecting a sample from said test environment, mixing said test sample or a fraction thereof with an artificial lung fluid sample, so as to obtain a liquid test sample, conducting one or a plurality of parallel oxidative potential quantification tests on said liquid test sample, determining the oxidizing potential of said test environment, wherein the method is conducted in an automated manner at the site of collection of said test sample, said method not including intermediate extraction of the collected sample, and leads to the determination of the OP in real-time.

2. The method according to claim 1, further comprising after the sampling step and before the mixing step, a step of fractionating the test sample into a gas fraction and/or a particulate fraction.

3. The method according to claim 1, wherein the artificial lung sample is a Gamble environment, optionally supplemented, with dipalmitoylphospatidylcholine (DPPC).

4. The method according to claim 1, wherein the test(s) for quantifying the oxidizing potential is (are) chosen from tests measuring the consumption by a test sample of an antioxidant species.

5. The method according to claim 4, wherein the antioxidant species is selected from the group consisting of ascorbic acid (AA), dithiothreitol (DTT), dichlorofluorescein (DCFH), gluthatione (GSH), and RTLF (respiratory tract lining fluid) mixture.

6. The method according to claim 1, wherein the method carries out the OP quantification test by measuring the depletion of ascorbic acid (AA) and the depletion of dithiothreitol (DTT).

7. The method according to claim 1, wherein the method is carried out under physiological conditions.

8. The method according to claim 1, wherein the mixing of the test sample or of a fraction thereof with the artificial lung fluid is carried out by nebulization.

9. A method of determining air pollution or emissions of gases and/or particles, said method comprising:

implementing the method according to claim 1, using a test sample taken from ambient atmospheric air or emissions of gases and/or particles to be tested; and correlating the OP obtained with the air quality or toxicity of the tested environment.

10. An instrument for implementing a method for measuring the oxidative potential (OP) of a test environment according to claim 1, comprising:

a module for collecting a test sample from the test environment;

a chamber for nebulizing the test sample or a fraction thereof with an artificial lung fluid sample, so as to form a liquid test sample;

at least one test module configured for reacting the liquid test sample obtained with a reagent;

a module for measuring the depletion of said reagent; and a module for calculating the OP.

11. The instrument according to claim 10, further comprising a system configured for feeding the test module(s):

with the liquid test sample from an outlet of the nebulizing chamber, with a reagent from a reagent storage tank.

12. The instrument according to claim 10, further comprising a plurality of test modules in parallel, each test module being configured for reacting the liquid test sample with a respective reagent.

13. The instrument according to claim 10, wherein said module for measuring the depletion of said reagent comprises an optical measurement module.

14. The instrument according to claim 10, further comprising a system configured for circulating a wash solution through the test module(s).

\* \* \* \* \*